(12) United States Patent
Seeboth et al.

(10) Patent No.: US 8,765,943 B2
(45) Date of Patent: *Jul. 1, 2014

(54) 1,2,4-TRIAZINE SUITABLE AS A VULCANIZATION ACCELERATOR AND METHOD FOR PRODUCING SAME

(75) Inventors: Nicolas Seeboth, Clermont-Ferrand (FR); Sergey Ivanov, Orekhovo-Zouevo (RU); Sergey Molkov, Tcheboksary (RU)

(73) Assignees: Compagnie Generale des Etablissements Michelin, Clermont-Ferrand (FR); Michelin Recherche et Technique S.A., Granges-Paccott (CH)

( * ) Notice: Subject to any disclaimer, the term of this patent is extended or adjusted under 35 U.S.C. 154(b) by 49 days.

This patent is subject to a terminal disclaimer.

(21) Appl. No.: 13/501,092

(22) PCT Filed: Oct. 8, 2010

(86) PCT No.: PCT/EP2010/065067
§ 371 (c)(1),
(2), (4) Date: Sep. 21, 2012

(87) PCT Pub. No.: WO2011/042521
PCT Pub. Date: Apr. 14, 2011

(65) Prior Publication Data
US 2013/0053559 A1    Feb. 28, 2013

(30) Foreign Application Priority Data
Oct. 8, 2009  (FR) ...................................... 09 57036

(51) Int. Cl.
*C07D 253/06*   (2006.01)
*C08L 77/00*    (2006.01)

(52) U.S. Cl.
USPC ........ 544/182; 544/180; 524/575.5; 525/182; 525/348

(58) Field of Classification Search
USPC ......... 524/575.5, 182; 525/348; 544/182, 180
See application file for complete search history.

(56) References Cited

U.S. PATENT DOCUMENTS 3,211,729 A * 10/1965 Siegrist et al. ................ 544/182
4,301,260 A * 11/1981 Wilder .......................... 525/348
2013/0053509 A1 * 2/2013 Veyland et al. ............ 524/575.5

* cited by examiner

*Primary Examiner* — Liam Heincer
*Assistant Examiner* — Marilou Lacap
(74) *Attorney, Agent, or Firm* — Cozen O'Connor

(57) ABSTRACT

A 1,2,4-triazine of formula (I):

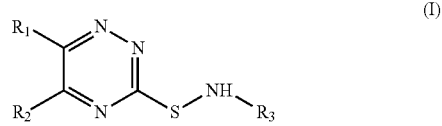

and its process of manufacture and use.

15 Claims, No Drawings

1,2,4-TRIAZINE SUITABLE AS A VULCANIZATION ACCELERATOR AND METHOD FOR PRODUCING SAME

RELATED APPLICATIONS

This is a U.S. national stage of application No. PCT/EP2010/065067, filed on Oct. 8, 2010. Priority is claimed on the following application: French Application No.: 0957036 filed on Oct. 8, 2009, the disclosure content of which is hereby incorporated here by reference.

FIELD OF THE INVENTION

The present invention relates to a specific triazine, to its process of preparation and to its use as vulcanization accelerator.

BACKGROUND OF THE INVENTION

The vulcanization of diene elastomers by sulphur is widely used in the rubber industry, in particular the tire industry. Use is made, in order to vulcanize diene elastomers, of a relatively complex vulcanization system comprising, in addition to the sulphur, a primary vulcanization accelerator, such as sulphenamides comprising a benzothiazole ring system, and also various secondary vulcanization accelerators or vulcanization activators, very particularly zinc derivatives, such as zinc oxide (ZnO) alone or used with fatty acids.

Such vulcanization accelerators, in order to be used in rubber compositions based on diene elastomers and on reinforcing fillers which can be used in particular for the manufacture of tires, have to induce sufficient crosslinking while retaining a delay phase (time necessary for the start of the vulcanization) which is correct, indeed even improved.

Vulcanization accelerators play a major role in the achievement of a delay phase (induction period) and it is known to a person skilled in the art that this parameter is very difficult to adjust. It is therefore particularly advantageous for a person skilled in the art to have a vulcanization accelerator which induces a lengthy delay phase which he can adjust, if desired, by the addition of additional accelerators.

SUMMARY OF THE INVENTION

The inventors have discovered that a specific triazine compound, 1,2,4-triazine, can be used as vulcanization accelerator and makes it possible to also improve the rheometric properties of a rubber composition using such a compound, without damaging the other properties of such a composition.

One aspect of the invention is directed to a 1,2,4-triazine of formula (I):

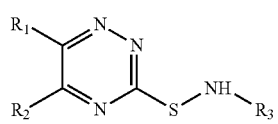

where
$R_1$ and $R_2$ independently represent H or a $C_1$-$C_{25}$ hydrocarbon group chosen from linear, branched or cyclic alkyl groups and aryl groups which are optionally interrupted by one or more heteroatoms, it being possible for $R_1$ and $R_2$ to together form a ring, $R_3$ represents:

a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Another aspect of the invention is directed to the use, as vulcanization accelerator, of a 1,2,4-triazine as defined above.

A further aspect of the invention is directed to a process for the preparation of a 1,2,4-triazine as defined above by oxidative coupling between a 1,2,4-triazine-3-thiol compound of following formula (A):

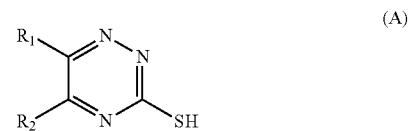

where $R_1$ and $R_2$ are as defined above, and a primary amine of formula $R_3NH_2$, where $R_3$ is as defined above, the oxidative coupling being carried out using a basic composition and an oxidizing compound.

DETAILED DISCUSSION

The invention and its advantages will be easily understood in the light of the description and implementational examples which follow.

I. Measurements and Tests Used

The rubber compositions in which the 1,2,4-triazine vulcanization accelerators are tested are characterized, after curing, as indicated below.

Rheometry

The measurements are carried out at 150° C. with an oscillating disc rheometer, according to Standard DIN 53529—part 3 (June 1983). The change in the rheometric torque, ΔTorque, as a function of time describes the change in the stiffening of the composition as a result of the vulcanization reaction. The measurements are processed according to Standard DIN 53529—part 2 (March 1983): $t_0$ is the induction period, that is to say the time necessary for the start of the vulcanization reaction; $t_\alpha$ (for example $t_{99}$) is the time necessary to achieve a conversion of α %, that is to say α % (for example 99%) of the difference between the minimum and maximum torques. The conversion rate constant, denoted K (expressed in $min^{-1}$), which is first order, calculated between 30% and 80% conversion, which makes it possible to assess the vulcanization kinetics, is also measured.

II. Conditions for the Implementation of the Invention

II-1. Triazine of the Invention

As explained above, the first subject-matter of the invention is a 1,2,4-triazine of following formula (I):

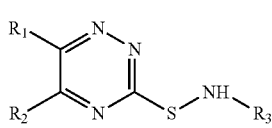

(I)

where
$R_1$ and $R_2$ independently represent H or a $C_1$-$C_{25}$ hydrocarbon group chosen from linear, branched or cyclic alkyl groups and aryl groups which are optionally interrupted by one or more heteroatoms, it being possible for $R_1$ and $R_2$ to together form a ring, $R_3$ represents:
  a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Cyclic alkyl group is understood to mean an alkyl group composed of one or more rings.

The heteroatom or heteroatoms can be a nitrogen, sulphur or oxygen atom.

According to a first embodiment, $R_1$ and $R_2$ independently represent H, a methyl group or a phenyl group.

Advantageously, $R_1$ or $R_2$ represent a phenyl group. Preferably, $R_2$ is a phenyl group and $R_1$ is a hydrogen.

$R_3$ can represent a cyclohexyl group or a tert-butyl group. Preferably, $R_3$ represents a tert-butyl group.

A preferred 1,2,4-triazine of formula (I) is that in which $R_1$ represents hydrogen, $R_2$ represents a phenyl group and $R_3$ represents a cyclohexyl group. Such a compound is 3-[(cyclohexylamino)thio]-5-phenyl-1,2,4-triazine (also known as N-cyclohexyl-S-(5-phenyl-1,2,4-triazin-3-yl)thiohydroxylamine).

Another preferred 1,2,4-triazine of formula (I) is that in which $R_1$ represents hydrogen, $R_2$ represents a phenyl group and $R_3$ represents a tert-butyl group. Such a compound is 3-[(t-butylamino)thio]-5-phenyl-1,2,4-triazine.

II-2. Synthetic Process

The 1,2,4-triazines of formula (I) can be prepared by oxidative coupling between
  a 1,2,4-triazine-3-thiol compound of following formula (A):

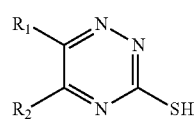

(A)

where $R_1$ and $R_2$ are as defined above, and
  a primary amine of formula $R_3NH_2$, where $R_3$ is as defined above,
the oxidative coupling being carried out using a basic composition and an oxidizing compound.

According to a first embodiment of the invention, the 1,2,4-triazines of formula (I) can be prepared according to a synthetic process comprising the following stages:
  the starting compound is 1,2,4-triazine-3-thiol of following formula (A):

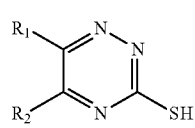

(A)

where $R_1$ and $R_2$ are as defined above,
it being possible for this 1,2,4-triazine-3-thiol to be obtained, without this being limiting, by condensation between a 1,2-dicarbonyl compound and thiosemicarbazide according to generic methods described, for example, in the Journal of Organic Chemistry, Vol. 52, No. 19, 1987, pp. 4280-4287, or by L. M. Mironovich and V. K. Promonenkov in the chapter entitled "1,2,4-Triazines" of volume 22 of the work Summary of science and technology. Organic Chemistry Series, edited in 1990 by Viniti, Moscow;
  the compound (A) is reacted with the basic composition, which can be an aqueous solution of an organic or inorganic base, for example an aqueous sodium hydroxide solution, then
  the primary amine of formula $R_3NH_2$, where $R_3$ is as defined above, is added to the reaction medium and the oxidative coupling is carried out in the presence of the oxidizing compound, which can, for example, be a halogen compound, such as chlorine, bromine, iodine, hypohalous acids or their alkali metal salts, such as, for example, sodium hypochlorite.

Preferably, $R_1$ represents hydrogen and $R_2$ represents a phenyl group.

Preferably, $R_3$ represents a cyclohexyl group.

According to a second embodiment of the invention, the 1,2,4-triazines of formula (I) can be prepared according to a synthetic process comprising the following stages:
a) primary amine of formula $R_3NH_2$ is reacted with the said oxidizing compound, then
b) a composition comprising the basic composition, the said compound of formula (A) and primary amine of formula $R_3NH_2$ is added to the reaction medium obtained in stage a).

Preferably, $R_1$ represents hydrogen and $R_2$ represents a phenyl group.

Preferably, $R_3$ represents a tert-butyl group.

The basic composition can be an aqueous solution of an organic or inorganic base, for example an aqueous sodium hydroxide solution.

The oxidizing compound can be chosen from halogen compounds, preferably chlorine, bromine, iodine and hypohalous acids and their alkali metal salts. Mention may in particular be made of sodium hypochlorite.

II-3. Use as Vulcanization Accelerator

As indicated above, the 1,2,4-triazine compound of the invention has an advantageous and industrial application as vulcanization accelerator. It can thus be used in a rubber composition for the manufacture of tires, based on one or more diene elastomers, on one or more reinforcing fillers and on a vulcanization system.

For such a use, the diene elastomer or elastomers is/are preferably chosen from the group of highly unsaturated diene elastomers consisting of polybutadienes (abbreviated to "BR"), synthetic polyisoprenes (IR), natural rubber (NR), butadiene copolymers, isoprene copolymers and the mixtures of these elastomers. Such copolymers are more preferably chosen from the group consisting of butadiene/stirene copolymers (SBR), isoprene/butadiene copolymers (BIR), isoprene/stirene copolymers (SIR) and isoprene/butadiene/stirene (SBIR) copolymers.

Furthermore, use may be made of any type of reinforcing filler known for its abilities to reinforce a rubber composition which can be used in the manufacture of tires, for example an organic filler, such as carbon black, a reinforcing inorganic filler, such as silica, or a blend of these two types of filler, in particular a blend of carbon black and silica.

The term "reinforcing inorganic filler" should be understood in the present patent application, by definition, as meaning any inorganic or mineral filler, whatever its colour or its origin (natural or synthetic), also known as "white filler", "clear filler", indeed even "non-black filler", in contrast to carbon black, capable of reinforcing by itself alone, without means other than an intermediate coupling agent, a rubber composition intended for the manufacture of tires, in other words capable of replacing, in its reinforcing role, a conventional tire-grade carbon black; such a filler is generally characterized, in a known way, by the presence of hydroxyl (—OH) groups at its surface.

Suitable in particular as reinforcing inorganic fillers are mineral fillers of siliceous type, in particular silica ($SiO_2$).

The vulcanization system proper is based on sulphur (or on a sulphur-donating agent) and on a primary vulcanization accelerator. Additional to this base vulcanization system are various known secondary vulcanization accelerators or vulcanization activators, such as zinc oxide, stearic acid or equivalent compounds, or guanidine derivatives (in particular diphenylguanidine).

The primary vulcanization accelerator must allow rubber compositions to crosslink within industrially acceptable times while retaining a minimum safety period ("scorch time") during which the compositions can be shaped without risk of premature vulcanization ("scorching").

The 1,2,4-triazine compound according to the invention can thus be used as vulcanization accelerator. It replaces, in all or in part, the normal compounds, in particular sulphenamides.

III. Examples of the Implementation of the Invention

III-1 3-[(Cyclohexylamino)thio]-5-phenyl-1,2,4-triazine

In the following examples, the invention is implemented with 3-[(cyclohexylamino)thio]-5-phenyl-1,2,4-triazine (compound B) of following formula:

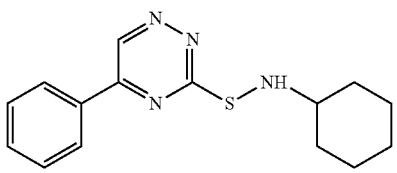 [SMILES: c1ccc(-c2cnnc(SNC3CCCCC3)n2)cc1]

III-1.1 Synthesis of the Triazine Compound

This compound is prepared from 5-phenyl-1,2,4-triazine-3-thiol and cyclohexylamine according to the following synthetic scheme:

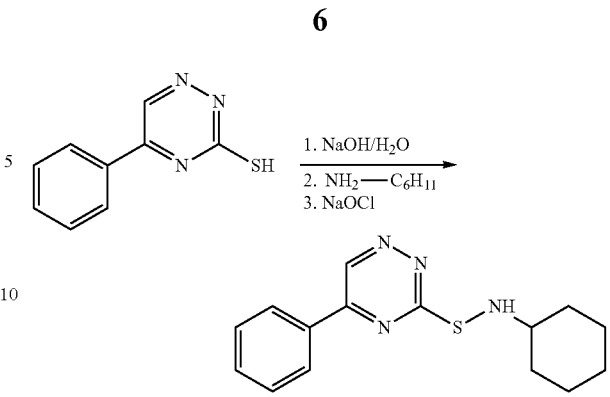

5-Phenyl-1,2,4-triazine-3-thiol (CAS number [15969-28-5]), is commercially available or can be obtained according to the procedures described in the following documents:

1. Daunis, J. et al.; Bulletin de la Société Chimique de France; 1969, 10; 3675-3678.
2. Joshi, K. C., Dubey, K. and Dandia, A., Heterocycles (1981), 16(9); 1545-1553.

Cyclohexylamine (107.6 g, 1.09 mol) is added to a solution of 5-phenyl-1,2,4-triazine-3-thiol (41.0 g, 0.22 mol) and sodium hydroxide (20.0 g, 0.50 mol) in water (700 ml). The mixture is cooled to a temperature of between 0 and −5° C. and then the aqueous NaOCl solution (4% active chlorine) (477 ml) is added dropwise over 30 minutes. The temperature of the reaction medium remains between 0 and −4° C. The reaction medium is subsequently stirred at a temperature of between 0 and 5° C. for from 1h 30 to 2 hours.

Petroleum ether (100 ml) is added and the reaction mixture is subsequently stirred at a temperature of between 0 and −4° C. for from 15 to 30 minutes. The precipitate is filtered off, washed with water (200 ml) and petroleum ether (50 ml) and finally dried under reduced pressure for from 2 to 3 hours.

A white solid (42.9 g, 0.15 mol, yield 68%) with a melting point of 125-127° C. is obtained.

The molar purity is greater than 97% ($^1$H NMR).

If the purity is insufficient, crystallization from ethyl acetate makes it possible to obtain the pure product.

The product is completely characterized by NMR. The chemical shifts obtained by $^1$H and $^{13}$C NMR in $d_6$ DMSO are given in the table below. Calibration is carried out with regard to DMSO (2.44 ppm in $^1$H and at 39.5 ppm in $^{13}$C).

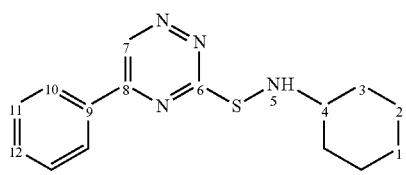

The results are shown in Table 1.

TABLE 1

| | No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| δ($^1$H) in ppm | 1.45 1.13 | 1.63 1.13 | 1.92 1.13 | 2.97 | 5.08 | / | 9.73 | / | / | 8.27 | 7.56 | 7.61 |

TABLE 1-continued

| | No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| $\delta(^{13}C)$ in ppm | 25.5 | 23.8 | 32.4 | 56.7 | / | 176.4 | 143.2 | 154.2 | 132.9 | 127.8 | 129.3 | 132.8 |

III-1.2. Use as Vulcanization Accelerator—Preparation of the Compositions

The procedure for the following tests is as follows: the diene elastomer or elastomers, the reinforcing filler or fillers and the optional coupling agent, followed, after kneading for from 1 to 2 minutes, by the various other ingredients, with the exception of the vulcanization system, are introduced into an internal mixer, 70% filled and having a starting vessel temperature of approximately 90° C. Thermomechanical working (nonproductive phase) is then carried out in one stage (total duration of the kneading equal to approximately 5 min), until a maximum "dropping" temperature of approximately 165° C. is reached. The mixture thus obtained is recovered and cooled, and then the vulcanization system (sulphur and triazine compound (or "CBS" for the comparative example)) is added on an external mixer (homofinisher) at 70° C., everything being mixed (productive phase) for approximately from 5 to 6 min.

The compositions thus obtained are subsequently calendered, either in the form of plaques (thickness of 2 to 3 mm) or thin sheets of rubber, for the measurement of their physical or mechanical properties, or in the form of profiled elements which can be used directly, after cutting out and/or assembling to the desired dimensions, for example as semifinished products for tires, in particular as tire treads.

III-1.3. Characterization Tests—Results

A—EXAMPLE 1

The object of this example is to compare the properties of a rubber composition comprising carbon black as predominant reinforcing filler, which can be used in the manufacture of a tire tread, comprising 3-[(cyclohexylamino)thio]-5-phenyl-1,2,4-triazine (compound B) as primary vulcanization accelerator (composition 2), with the properties of a rubber composition comprising N-cyclohexyl-2-benzothiazole-sulphenamide ("CBS") (composition 1).

The formulations of the compositions are given in Table 2. The amounts are expressed as parts per 100 parts by weight of elastomer (phr).

TABLE 2

| | Composition 1 | Composition 2 |
|---|---|---|
| NR (1) | 40 | 40 |
| BR (2) | 20 | 20 |
| SBR (3) | 40 | 40 |
| N234 (4) | 54 | 54 |
| Paraffin | 1 | 1 |
| 6-PPD (5) | 2 | 2 |
| Stearic acid | 2 | 2 |
| ZnO | 2.7 | 2.7 |
| Sulphur | 1.1 | 1.1 |

TABLE 2-continued

| | Composition 1 | Composition 2 |
|---|---|---|
| Vulcanization accelerator | 1.1* | 1.23** |

*CBS ("Santocure CBS" from Flexsys)
**3-[(cyclohexylamino)thio]-5-phenyl-1,2,4-triazine
(1) Natural rubber
(2) Polybutadiene with 0.7% of 1-2; 1.7% of trans-1,4-; 98% of cis-1,4- (Tg = −105° C.) (molar %)
(3) Butadiene/stirene copolymer SSBR (SBR prepared in solution) with 25% of stirene, 59% of 1,2-polybutadiene units and 20% of trans-1,4-polybutadiene units (Tg = −24° C.) (molar %); level expressed as dry SBR (SBR extended with 9% by weight of MES oil, i.e. a total of SSBR + oil equal to 76 phr)
(4) Carbon black N 234
(5) Antioxidant 6-p-phenylenediamine The rubber composition 2 comprising 3-[(cyclohexylamino)thio]-5-phenyl-1,2,4-triazine is identical to composition 1, it being understood that the CBS is replaced with an isomolar amount of 3-[(cyclohexylamino)thio]-5-phenyl-1,2,4-triazine.

The rheometric properties at 150° C. are given in Table 3.

TABLE 3

| | Composition 1 (CBS) | Composition 2 (Compound B) |
|---|---|---|
| Rheo. prop. (DIN) | | 150° C. |
| Δtorque(dN · m) | 8.5 | 8.7 |
| k(min$^{-1}$) | 0.416 | 0.353 |
| t$_0$(min) | 6.0 | 8.6 |

The rheometric properties obtained for composition 2 comprising 3-[(cyclohexylamino)thio]-5-phenyl-1,2,4-triazine are equivalent to those obtained for composition 1 comprising CBS. It is even noted that the delay phase (induction period t$_0$) is longer in the case of composition 2 comprising 3-[(cyclohexylamino)thio]-5-phenyl-1,2,4-triazine, which is advantageous.

It is furthermore noted that compound B, and the compounds of formula (I) in general, advantageously replace, with regard to the environmental impact, sulphenamides comprising a mercaptobenzothiazole ring system, by not generating, in contrast to the latter, mercaptobenzothiazole on decomposing during the curing.

B—EXAMPLE 2

The object of this example is to compare the properties of a rubber composition comprising silica as predominant reinforcing filler, which can be used in the manufacture of a tire tread, comprising 3-[(cyclohexylamino)thio]-5-phenyl-1,2,4-triazine (compound B) as primary vulcanization accelerator (composition 4), with the properties of a rubber composition comprising N-cyclohexyl-2-benzothiazolesulphenamide ("CBS") (composition 3).

The formulations of the compositions are given in Table 4. The amounts are expressed as parts per 100 parts by weight of elastomer (phr).

TABLE 4

|  | Composition 3 | Composition 4 |
|---|---|---|
| BR (1) | 28 | 28 |
| SBR (2) | 79.2 | 79.2 |
| N234 (3) | 4 | 4 |
| Silica (4) | 82 | 82 |
| 6-PPD (5) | 1.9 | 1.9 |
| MES (6) | 4.8 | 4.8 |
| Antiozone wax | 1.5 | 1.5 |
| Plasticizing resin (7) | 20 | 20 |
| Coupling agent (8) | 6.56 | 6.56 |
| Stearic acid | 2 | 2 |
| DPG (9) | 1.54 | 1.54 |
| ZnO | 1.5 | 1.5 |
| Sulphur | 1.2 | 1.2 |
| Vulcanization accelerator | 1.9* | 2.12** |

*CBS ("Santocure CBS" from Flexsys)
**3-[(cyclohexylamino)thio]-5-phenyl-1,2,4-triazine
(1) Polybutadiene with 0.7% of 1-2; 1.7% of trans-1,4-; 98% of cis-1,4- (Tg = −105° C.) (molar %)
(2) Butadiene/stirene copolymer SSBR (SBR prepared in solution) with 25% of stirene, 59% of 1,2-polybutadiene units and 20% of trans-1,4-polybutadiene units (Tg = −24° C.) (molar %); level expressed as dry SBR (SBR extended with 9% by weight of MES oil, i.e. a total of SSBR + oil equal to 76 phr)
(3) Carbon black N 234
(4) Silica "Zeosil 1165MP" from Rhodia, "HDS" type (BET and CTAB: approximately 160 m²/g);
(5) Antioxidant 6-p-phenylenediamine
(6) Plasticizing oil "Medium Extracted Solvates" (Catenex SNR from Shell)
(7) Aliphatic resin (pure C5) "Hikorez A-1100", sold by Kolon
(8) Coupling agent bis(3-triethoxysilylpropyl) tetrasulphide TESPT ("Si69" from Degussa)
(9) Diphenylguanidine (Perkacit DPG from Flexsys)

The rubber composition 4 comprising 3-[(cyclohexylamino)thio]-5-phenyl-1,2,4-triazine is identical to composition 3, it being understood that the CBS is replaced with an isomolar amount of 3-[(cyclohexylamino)thio]-5-phenyl-1,2,4-triazine.

The rheometric properties at 150° C. are given in Table 5.

TABLE 5

|  | Composition 3 (CBS) | Composition 4 (Compound B) |
|---|---|---|
| Rheo. prop. (DIN) | 150° C. | |
| Δtorque(dN·m) | 11.9 | 12.2 |
| k(min⁻¹) | 0.064 | 0.052 |
| t₀(min) | 4.9 | 6.9 |

The rheometric properties obtained for composition 4 containing 3-[(cyclohexylamino)thio]-5-phenyl-1,2,4-triazine are equivalent to those obtained for composition 1 comprising CBS. It is even noted that the delay phase (induction period $t_0$) is longer in the case of composition 4 comprising 3-[(cyclohexylamino)thio]-5-phenyl-1,2,4-triazine, which is advantageous.

III-2. 3-[(t-Butylamino)thio]-5-phenyl-1,2,4-triazine

The process for the preparation of 3-[(t-butylamino)thio]-5-phenyl-1,2,4-triazine (compound C), of following formula:

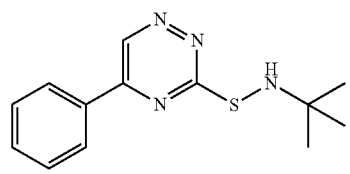 [SMILES: CC(C)(C)NSc1nncc(-c2ccccc2)n1]

is described here.

The preparation of this sulphenamide is based on an oxidative coupling between 5-phenyl-1,2,4-triazine-3-thiol and tert-butylamine, according to the following synthetic scheme:

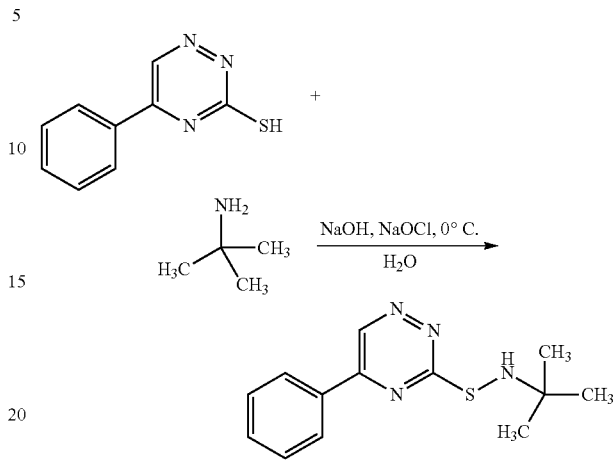

An aqueous NaOCl solution (136 ml, assaying 17.4% active chlorine) is added dropwise over 45 min to 350 ml of tert-butylamine maintained between −10° C. and −5° C. (temperature of the bath). Throughout the duration of the addition, the temperature of the bath is maintained between −10° C. and −5° C. A solution of 5-phenyl-1,2,4-triazine-3-thiol (40.30 g, 0.213 mol; purity: approximately 98 molar %, determined by NMR), sodium hydroxide (16.96 g, 0.424 mol) and tert-butylamine (50 ml) in water (350 ml) is added dropwise over 90 min to this solution maintained at 0° C. The temperature of the reaction medium remains maintained between 0 and +6° C. The reaction medium is subsequently stirred at a temperature of between +5 and +10° C. for one hour and then at ambient temperature for 2 hours.

Subsequently, this medium is diluted with 0.7 l of cold water (approximately 4° C.). This suspension is stirred for a further 10 minutes and then the precipitate of the product obtained is filtered off, washed on the filter with water (10 times 500 ml) and then dried under air for 48 h. A yellow solid (49.5 g, 0.190 mol, yield 89%) with a melting point of 73° C. is obtained. The molar purity, determined by $^1$H NMR, is 95%.

The reaction is monitored by thin layer chromatography: $Rf_{product}=0.52$, $Rf_{disulphide\ impurity}=0.61$ (characteristics of the TLC: SiO$_2$; EtOAc:heptane=1:1; visualization by UV and I$_2$).

The product is completely characterized by NMR. The chemical shifts obtained by $^1$H and $^{13}$C NMR in d$_6$-DMSO are given in the table below. Calibration is carried out with regard to DMSO (2.44 ppm in $^1$H and at 39.5 ppm in $^{13}$C).

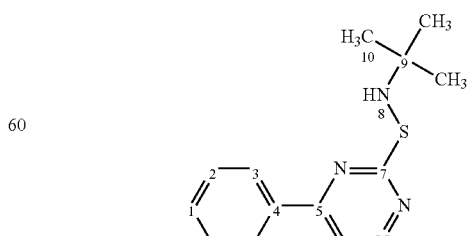

The results are given in Table 6.

TABLE 6

| | No. | | | | | | | | | |
|---|---|---|---|---|---|---|---|---|---|---|
| | 1 | 2 | 3 | 4 | 5 | 6 | 7 | 8 | 9 | 10 |
| δ $^1$H ppm | 7.59 | 7.56 | 8.29 | — | — | 9.72 | — | 4.87 | — | 1.11 |
| δ $^{13}$C ppm | 132.7 | 128.9 | 127.7 | 129.7 | 153.7 | 142.9 | 177.0 | — | 54.3 | 29.1 |

The invention claimed is:

1. 1,2,4-Triazine of formula (I):

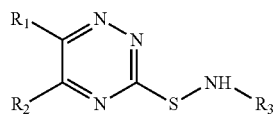

(I)

where $R_1$ and $R_2$ independently represent H or a $C_1$-$C_{25}$ hydrocarbon group chosen from linear, branched or cyclic alkyl groups and aryl groups which are optionally interrupted by one or more heteroatoms, it being possible for $R_1$ and $R_2$ to together form a ring, $R_3$ represents:

a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

2. The 1,2,4-Triazine according to claim 1, wherein $R_1$ and $R_2$ independently represent H, a methyl group or a phenyl group.

3. The 1,2,4-Triazine according to claim 2, wherein $R_1$ or $R_2$ represent a phenyl group.

4. The 1,2,4-Triazine according to claim 3, wherein $R_1$ represents a hydrogen and $R_2$ is a phenyl group.

5. The 1,2,4-Triazine according to claim 1, wherein $R_3$ represents a cyclohexyl group or a tert-butyl group.

6. The 1,2,4-Triazine according to claim 1, wherein $R_3$ represents a tert-butyl group.

7. A process for the preparation of a 1,2,4-triazine according to claim 1, by oxidative coupling between a 1,2,4-triazine-3-thiol compound of following formula (A):

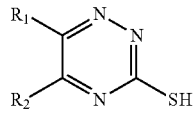

(A)

where $R_1$ and $R_2$ are as defined in claim 1, and a primary amine of formula $R_3NH_2$, where $R_3$ is as defined in claim 1, the oxidative coupling being carried out using a basic composition and an oxidizing compound.

8. The process according to claim 7, comprising the steps of:

the compound (A) is reacted with the said basic composition, then the primary amine of formula $R_3NH_2$ is added to the reaction medium, then the oxidative coupling is carried out by addition of the oxidizing compound.

9. The process according to claim 7, comprising the steps of:

a) primary amine of formula $R_3NH_2$ is reacted with the oxidizing compound, then b) a composition comprising the basic composition, the compound of formula (A) and primary amine of formula $R_3NH_2$ is added to the reaction medium obtained in stage a).

10. The process according to claim 9, wherein $R_3$ is a tert-butyl group.

11. The process according to claim 7, wherein the basic composition is an aqueous solution of an organic or inorganic base.

12. The process according to claim 11, wherein the inorganic base is sodium hydroxide.

13. The process according to claim 7, wherein the oxidizing compound is chosen from halogen compounds, preferably chlorine, bromine, iodine and hypohalous acids and their alkali metal salts.

14. The process according to claim 13, wherein the oxidizing compound is sodium hypochlorite.

15. A process for preparing a composition based on one or more diene elastomers, on one or more reinforcing fillers and on a vulcanization system, comprising incorporating as a vulcanization accelerator a 1,2,4-triazine as defined in claim 1.

* * * * *